(12) United States Patent
Van Wiltenburg et al.

(10) Patent No.: US 8,410,314 B1
(45) Date of Patent: Apr. 2, 2013

(54) METHOD OF SYNTHESIS

(75) Inventors: Jimmy Van Wiltenburg, Noordhorn (NL); Rene La Crois, Uithuizermeeden (NL)

(73) Assignee: BCS Business Consulting Services PTE Ltd., Faber Hse (SG)

( * ) Notice: Subject to any disclaimer, the term of this patent is extended or adjusted under 35 U.S.C. 154(b) by 102 days.

(21) Appl. No.: 13/134,920

(22) Filed: Jun. 20, 2011

Related U.S. Application Data

(60) Provisional application No. 61/398,155, filed on Jun. 21, 2010.

(51) Int. Cl.
*C07C 45/00* (2006.01)
(52) U.S. Cl. ........................................ 568/346; 568/348
(58) Field of Classification Search .................. 568/346, 568/348
See application file for complete search history.

(56) References Cited

U.S. PATENT DOCUMENTS

| | | |
|---|---|---|
| 4,689,345 A | 8/1987 | Kasha et al. |
| 4,689,349 A | 8/1987 | Kasha et al. |
| 5,264,619 A | 11/1993 | Ford |

OTHER PUBLICATIONS

Izawa et al.; Enantioselective Deprotonation of the Monoacetals of Bicyclo[3.3.0]OCTAN-3, 7-Dione. An Approach to the Asymmetric Synthesis of Chiral Synthons for Carbacyclins; Tetrahedron Letters, vol. 30, No. 51, pp. 7221-7224, 1989.

Mulzer el al., "Stereocontrolled synthesis of all eight stereoisomers of the putative anti-androgen cyoctol," Tetrahedron 60:9599-9614 (2004).

Petzoldt et al. Mikrobiologische und Enzymatische Reaktionsstufen in der Syntheswe von Prostacyclin-Analoga; Liebigs Ann. Chem 1990, 1087-1091.

*Primary Examiner* — Sikarl Witherspoon
(74) *Attorney, Agent, or Firm* — TraskBritt, P.C.

(57) ABSTRACT

Described is a method of synthesizing 6-(5-ethoxyhept-1-yl)bicyclo[3.3.0]octan-3-one by reacting 3-(5-ethoxyhept-1-yl)cyclopentene with dichloroketene. The resulting reaction products are reacted with acetic acid and zinc to produce 4-(5-ethoxyhept-1-yl)bicyclo[3.2.0]heptan-6-one and 4-(5-ethoxyhept-1-yl)bicyclo[3.2.0]heptan-7-one, which are reacted with trimethylsulfonium iodide to produce 2-(5-ethoxyhept-1-yl)spiro[bicyclo[3.2.0]heptane-6,2'-oxirane] and 4-(5-ethoxyhept-1-yl)spiro-[bicyclo-[3.2.0] heptane-6,2'-oxirane]. Lithium iodide is reacted with 2-(5-ethoxyhept-1-yl)spiro[bicyclo[3.2.0]heptane-6,2'-oxirane] and 4-(5-ethoxyhept-1-yl)spiro-[bicyclo-[3.2.0]heptane-6,2'-oxirane] to produce 6-(5-ethoxyhept-1-yl)bicyclo[3.3.0]octan-3-one. A method of synthesizing 6-(5-methoxyhept-1-yl)bicyclo[3.3.0]octan-3-one is also described.

10 Claims, 2 Drawing Sheets

US 8,410,314 B1

METHOD OF SYNTHESIS

CROSS-REFERENCE TO RELATED APPLICATION

This application claims the benefit under 35 U.S.C. §119(e) of U.S. Provisional Patent Application Ser. No. 61/398,155, filed Jun. 21, 2010, the disclosure of which is incorporated herein by this reference in its entirety.

TECHNICAL FIELD

The invention relates generally to a method of synthesizing a chemical compound, such as a method of synthesizing 6-(5-ethoxyhept-1-yl)bicyclo[3.3.0]octan-3-one or 6-(5-methoxyhept-1-yl)bicyclo[3.3.0]octan-3-one.

BACKGROUND

The chemical compound 6-(5-ethoxyhept-1-yl)bicyclo[3.3.0]octan-3-one (also known as ethoxyheptyl bicyclooctanone or ETHOCYN®) is a non-steroidal compound that penetrates into the dermis. CYOCTOL™ or 6-(5-methoxyhept-1-yl)bicyclo[3.3.0]octan-3-one is a similar compound. These compounds competitively inhibit intercellular dihydrotestosterone (DHT) receptor binding in fibroblasts derived from cutaneous tissues and has been investigated for treatment of DHT-mediated medical disorders, such as acne vulgaris, hirsuitism, androgenetic alopecia, and keloid scars.

The synthesis of 6-(5-ethoxyhept-1-yl)bicyclo[3.3.0]octan-3-one is complex due to, e.g., the compound's bicyclic structure, which includes four chiral centers. The synthesis includes multiple reactions, some of which are expensive or dangerous. One of the reactions includes a ring expansion reaction using etheral diazomethane, which is produced from DIAZALD® (N-methyl-N-nitroso-p-toluenesulfonamide) and ethanolic potassium hydroxide. The diazomethane reaction is highly toxic and dangerous, due to the explosive potential of the reaction. Methods of synthesizing 6-(5-ethoxyhept-1-yl)bicyclo[3.3.0]octan-3-one and derivatives are described in U.S. Pat. No. 4,689,349 to Kasha et al., the disclosure of which is incorporated by reference herein in its entirety. Methods of synthesizing a derivative of 6-(5-ethoxyhept-1-yl)bicyclo[3.3.0]octan-3-one, (6-(5-methoxyhept-1-yl)bicyclo[3.3.0]octan-3-one or CYOCTOL™), are also putatively described in Mulzer et al., "Stereocontrolled synthesis of all eight stereoisomers of the putative anti-androgen cyoctol," Tetrahedron 60:9599-9614 (2004).

BRIEF SUMMARY

Disclosed is a method of synthesizing a compound, such as 6-(5-ethoxyhept-1-yl)bicyclo[3.3.0]octan-3-one or methoxyheptyl bicyclooctanone, from 3-(5-ethoxyhept-1-yl)cyclopentene or other starting material. Such a method comprises reacting 3-(5-ethoxyhept-1-yl)cyclopentene with dichloroketene to form a first mixture comprising 7,7-dichloro-4-(5-ethoxyhept-1-yl)bicyclo[3.2.0]heptan-6-one and 6,6-dichloro-4-(5-ethoxyhept-1-yl)bicyclo[3.2.0]-heptan-7-one. The first mixture is reacted with acetic acid and zinc to form a second mixture comprising 4-(5-ethoxyhept-1-yl)bicyclo[3.2.0]heptan-6-one and 4-(5-ethoxyhept-1-yl)bicyclo-[3.2.0]heptan-7-one. The second mixture is reacted with trimethylsulfonium iodide to form a third mixture comprising 2-(5-ethoxyhept-1-yl)spiro[bicyclo[3.2.0]heptane-6,2'-oxirane]. The third mixture is reacted with lithium iodide to form 6-(5-ethoxyhept-1-yl)bicyclo[3.3.0]octan-3-one.

DETAILED DESCRIPTION

A method of synthesizing 6-(5-ethoxyhept-1-yl)bicyclo[3.3.0]octan-3-one is disclosed. The method of the invention provides a safer and less expensive manner of producing 6-(5-ethoxyhept-1-yl)bicyclo[3.3.0]octan-3-one. The 6-(5-ethoxyhept-1-yl)bicyclo[3.3.0] octan-3-one synthesized by the method of the invention may be produced at a good yield and have a purity suitable for use in a composition, such as a pharmaceutical composition or a cosmetic composition.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the invention and such term is used in preference to the more restrictive term "is" so as to avoid any implication that other, compatible materials, structures, features and methods usable in combination therewith should, or must be, excluded.

Figure 1:
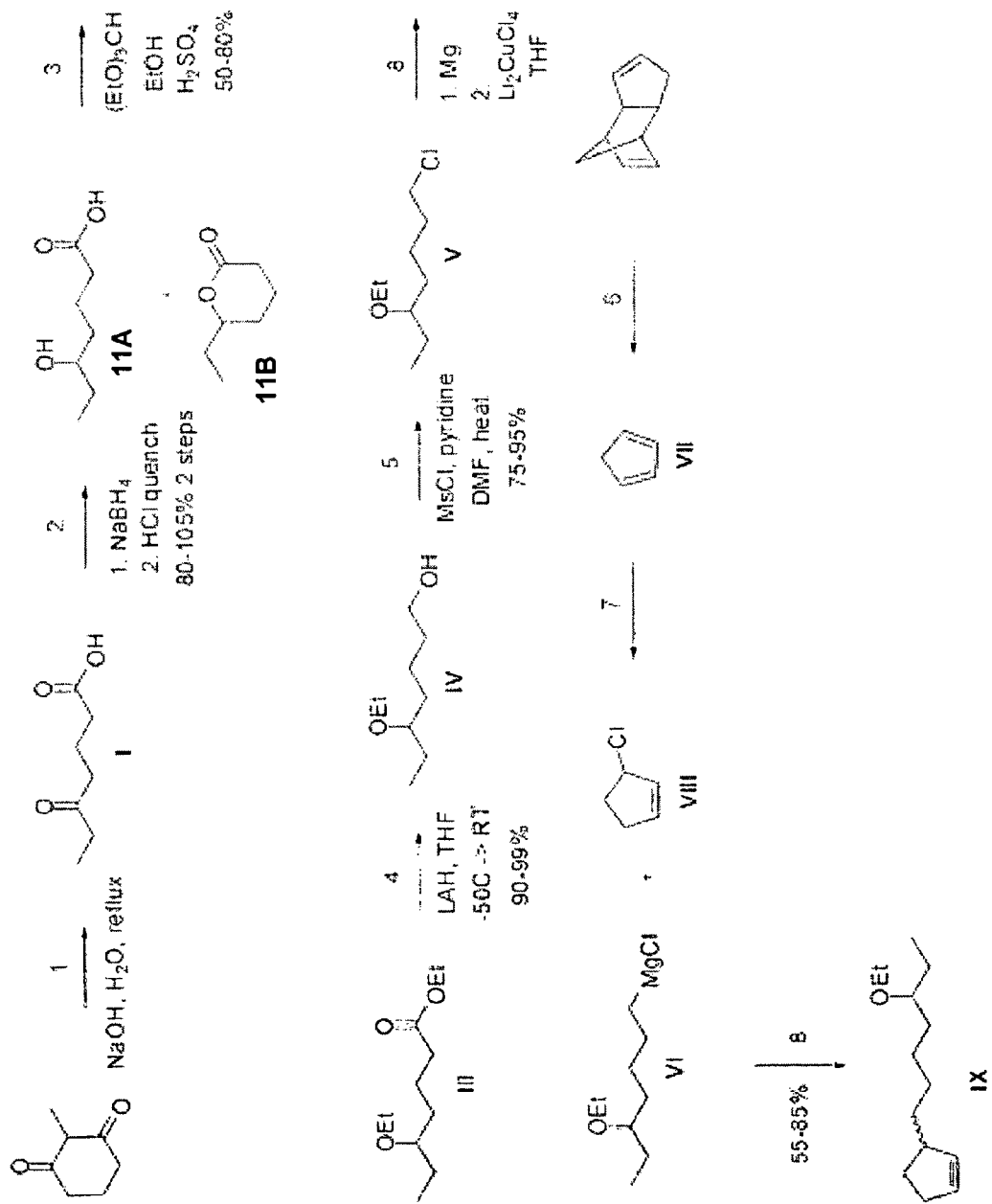
FIG. 1 illustrates the synthesis of 3-(5-ethoxyhept-1-yl)cyclopentene from 2-methyl-1,3-cyclohexanedione.
Figure 2:
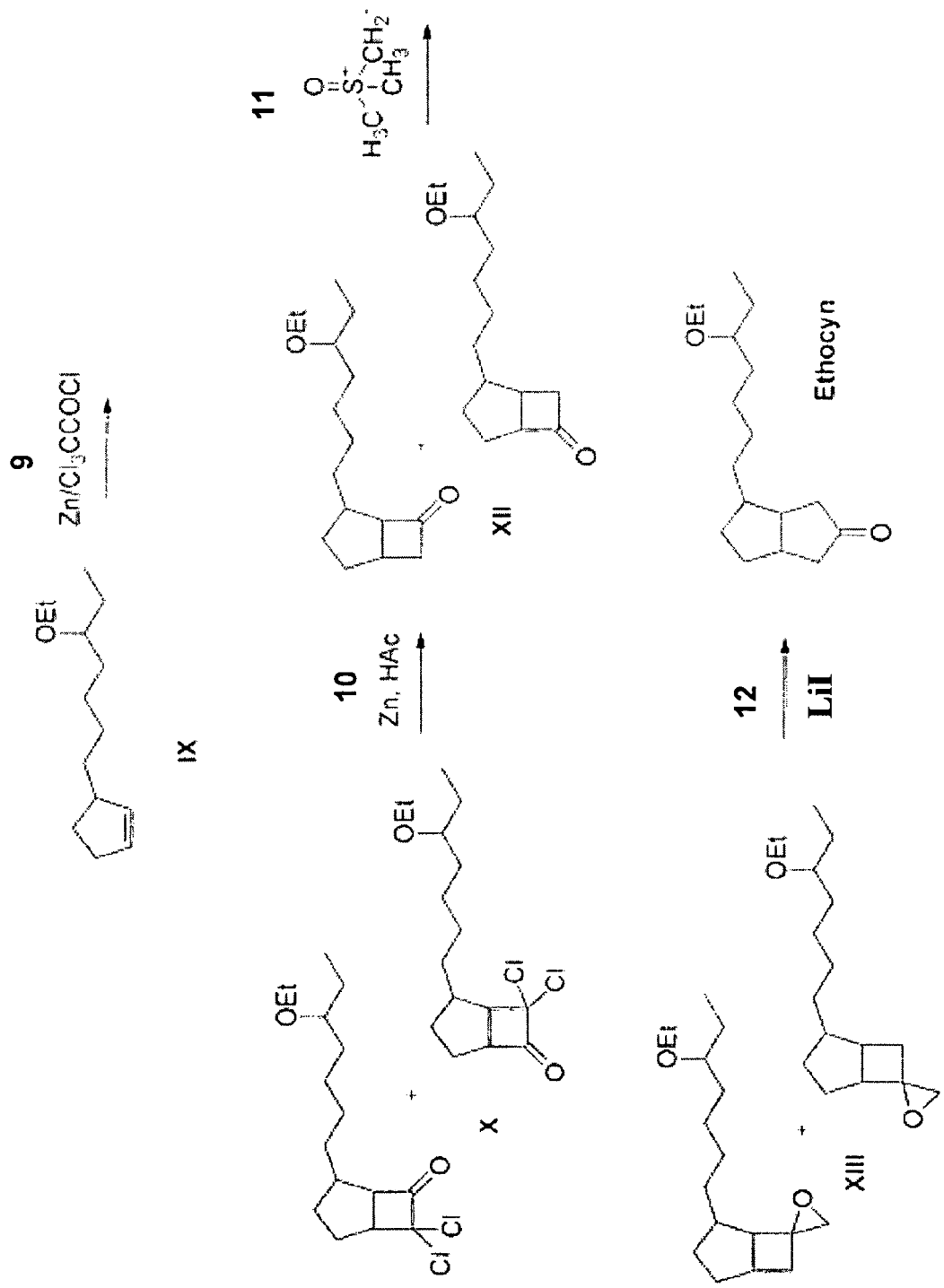
FIG. 2 illustrates the synthesis of 6-(5-ethoxyhept-1-yl)bicyclo[3.3.0]octan-3-one from 3-(5-ethoxyhept-1-yl)cyclopentene according to an embodiment of the invention.

The compound 6-(5-ethoxyhept-1-yl)bicyclo[3.3.0]octan-3-one may be synthesized as described in FIGS. 1 and 2. FIG. 1 describes the synthesis of 3-(5-ethoxyhept-1-yl)cyclopentene (Compound IX) from 2-methyl-1,3-cyclohexanedione. FIG. 2 describes the synthesis of 6-(5-ethoxyhept-1-yl)bicyclo[3.3.0]octan-3-one from Compound IX.

As shown in Reactions 1 and 2 of FIG. 1, the 2-methyl-1,3-cyclohexanedione may be reacted with sodium hydroxide and sodium borohydride in water, producing 5-hydroxyheptanoic acid (Compound IIA) and delta-lactone (Compound IIB) at a yield of from approximately 85% to approximately 105%. All percentages and ratios used herein are by weight of the total composition unless otherwise indicated or the context indicates otherwise. The 2-methyl-1,3-cyclohexanedione may be purchased from a chemical supply company, such as from Sigma-Aldrich Co. (St Louis, Mo.). The hydrolysis in Reaction 1 produces Compound I, a keto acid, in high yield. Sodium borohydride reduction of Compound I, followed by an acid quench produces a mixture of Compound IIA and Compound IIB, with Compound IIB being the predominant form. The carbonyl groups of Compound I may be reduced by the sodium borohydride, resulting in a racemic mixture of R and S enantiomers at the C-5 position of Compound IIA and at the C-6 position of the Compound IIB.

Compounds IIA and IIB may be reacted with triethyl orthoformate (TEOF), ethanol, and a sulfuric acid catalyst to produce ethyl-5-ethoxy-heptanoate (Compound III), as shown in Reaction 3. Each of Compounds IIA and IIB react with the indicated reagents to form the same product, Compound III. Compound III may be produced at a yield of from approximately 50% to approximately 80%. Compound III may be purified, such as by distillation, before additional reactions are conducted.

As shown in Reaction 4, Compound III may be reacted with lithium aluminum hydride (LAH) in tetrahydrofuran (THF) to produce 5-ethoxyheptanol (Compound IV). Compound IV may be produced at a yield of from approximately 90% to approximately 99%. The reaction may be conducted at a temperature of from approximately −50° C. to approximately room temperature (from approximately 20° C. to approximately 25° C.). To control the reaction, in some embodiments, the reaction is conducted at room temperature. As shown in Reaction 5, Compound IV may be reacted with methanesulfonyl chloride (MSCl) and pyridine in dimethylformamide (DMF) to produce 1-chloro-5-ethoxyheptane (Compound V) at a yield of from approximately 75% to approximately 95%.

As shown in Reactions 6-8, Compound V may be reacted with magnesium metal to form a Grignard salt, 5-ethoxyheptyl magnesium chloride (Compound VI), which is reacted with dilithium tetrachlorocuprate to form a dilithio cuprate complex. The dilithio cuprate complex may be coupled with 3-chlorocyclopentene (Compound VIII) to form 3-(5-ethoxy-hept-1-yl)cyclopentene (Compound IX) at a yield of from approximately 55% to approximately 85%. Compound VIII may be synthesized from cyclopentene (Compound VII), which is synthesized from dicyclopentadiene, as indicated in Reactions 6 and 7. The dicyclopentadiene may be purchased from a chemical supply company, such as from Sigma-Aldrich Co. (St Louis, Mo.). Thermal cracking and distillation of the dicyclopentadiene produces the monomeric cyclopentadiene, which is treated with hydrochloric acid to afford Compound VIII.

Each of Compounds I-IX produced in Reactions 1-8 may be worked up, purified, and isolated before proceeding to the next reaction. Compounds I-IX may be worked up, purified, and isolated by conventional techniques, which are not described in detail herein. In some embodiments, Compounds I-IX may be synthesized by the methods described in the incorporated U.S. Pat. No. 4,689,349 to Kasha et al.

Referring to FIG. 2, Compound IX may be reacted with dichloroketene, as shown in Reaction 9. The dichloroketene is generated in situ from trichloroacetyl chloride and zinc. The cycloaddition of dichloroketene to Compound IX produces a mixture of exo and endo 7,7-dichloro-4-(5-ethoxyhept-1-yl)bicyclo[3.2.0]heptan-6-one and exo and endo 6,6-dichloro-4-(5-ethoxyhept-1-yl)bicyclo[3.2.0]heptan-7-one, which is collectively referred to herein as Compound X. Reaction 9 produces both isomers of Compound X in substantially similar amounts. To produce Compound X, Compound IX may be dissolved in an organic solvent, such as diethyl ether. However, other organic solvents may be used, such as dimethylsulfoxide (DMSO), dimethylform-amide (DMF), acetonitrile, tetrahydrofuran, and any similar solvents. Zinc powder may be added to the solution of Compound IX. For every mole equivalent of Compound IX, from approximately 1.0 mole equivalent to approximately 3.0 mole equivalents of the zinc powder may be used in Reaction 9, such as from approximately 1.4 mole equivalents to approximately 1.8 mole equivalents. In certain embodiments, approximately 1.6 mole equivalents of zinc powder are used per mole equivalent of Compound IX. The mixture of zinc powder and the solution of Compound IX may be heated to a temperature just below the reflux temperature of the organic solvent. Trichloroacetyl chloride may be diluted with an organic solvent, such as diethyl ether, and the trichloroacetyl chloride solution added slowly to the mixture of zinc powder and the solution of Compound IX. However, other organic solvents may be used. For every mole equivalent of Compound IX, the trichloroacetyl chloride may be used in Reaction 9 at from approximately 1.0 mole equivalents to approximately 3.0 mole equivalents, such as from approximately 1.2 mole equivalents to approximately 1.6 mole equivalents. In certain embodiments, approximately 1.4 mole equivalents of trichloroacetyl chloride are used per mole equivalent of Compound IX. During the addition, the reaction mixture may start refluxing vigorously. The trichloroacetyl chloride solution may be added to the mixture of zinc powder and the solution of Compound IX over a time period of from approximately one hour to approximately two hours. Following the addition of the trichloroacetyl chloride solution, the reaction mixture may be mixed under reflux for an amount of time sufficient for the reaction to proceed to completion, such as from approximately ten minutes to approximately sixty minutes. The reaction mixture may then be cooled, filtered, subjected to at least one liquid:liquid extraction, dried, filtered, concentrated, and purified to produce Compound X as a colorless oil. By way of example, the reaction mixture may be cooled to room temperature and filtered through diatomaceous earth, such as diatomaceous earth available under the CELITE® trade name. The filter cake may be rinsed with an organic solvent, such as diethyl ether. However, other organic solvents may be used. The organic solvent layers may be combined and washed, such as with water. The organic phase layer may then be stirred with a saturated aqueous solution of sodium bicarbonate ($NaHCO_3$), such as for approximately one hour. After separation of the organic and aqueous phase layers, the organic layer may be washed with brine, dried over sodium sulfate ($Na_2SO_4$), filtered through silica, and concentrated in vacuo. The resulting residue may be purified, such as by bulb to bulb distillation, to produce Compound X as a colorless oil.

As shown in Reaction 10, Compound X may be reacted with acetic acid and zinc to produce a mixture of exo and endo 4-(5-ethoxyhept-1-yl)bicyclo[3.2.0]heptan-6-one and 4-(5-ethoxyhept-1-yl)bicyclo[3.2.0]heptan-7-one, which is collectively referred to herein as Compound XII. Reaction 10 produces both isomers of Compound XII in substantially similar amounts. Compound X may be used in Reaction 10 in crude form, i.e., without distillation, which reduces the decomposition of Compound X. It is believed that heating for distillation (at a temperature of greater than 200° C.) may cause decomposition of Compound X due to the presence of zinc or acid chloride derived residues remaining after Reaction 9. In Reaction 10, the zinc may be added portion-wise to a solution of Compound X in acetic acid. An excess of the zinc relative to Compound X may be used. By way of example, from approximately 2 mole equivalents to approximately 12 mole equivalents of zinc may be used per mole equivalent of Compound X, such as from approximately 5 mole equivalents to approximately 10 mole equivalents. In certain embodiments, the zinc is used at approximately 9.8 mole equivalents per mole equivalent of Compound X. The zinc may be added to the solution of Compound X at a temperature of from approximately 10° C. to approximately 20° C. After the addition of the zinc, which causes the temperature of the reaction to increase, the reaction mixture may be mixed, such as for approximately one hour. The reaction mixture may be filtered, concentrated, subjected to at least one liquid:liquid extraction, dried, filtered, concentrated, and purified to produce Compound XII as a colorless oil. By way of example, the reaction mixture may be filtered through diatomaceous earth available under the CELITE® trade name, and the filtrate concentrated in vacuo, producing a residue. The resulting residue may be partitioned between heptanes and water. The organic and aqueous phase layers may be separated and the organic phase layer washed with an aqueous solution of $NaHCO_3$/brine. The organic phase layer may be dried over Na$_2$SO$_4$, and an organic solvent, such as ethyl acetate, added. However, other organic solvents may be used. The reaction mixture may be filtered, such as through silica, and the filtrate concentrated. The resulting residue may be purified, such as by bulb to bulb distillation, to produce Compound XII as a colorless oil. Compound XII may be produced at a yield of greater than approximately 55%. Compound XII is stable and may be distilled.

As shown in Reaction 11, Compound XII may be reacted with trimethylsulfonium iodide to produce a mixture of 4-(5-ethoxyhept-1-yl)spiro[bicyclo[3.2.0]heptane-6,2'-oxirane] and 2-(5-ethoxyhept-1-yl)spiro[bicyclo[3.2.0]heptane-6,2'-oxirane], which is collectively referred to herein as Compound XIII. Reaction 11 produces both isomers of Compound XIII in substantially similar amounts. Compound XIII is thermally stable and may be isolated. Sodium hydride may be added to an organic solvent, such as dimethylsulfoxide (DMSO), heated to a temperature of from approximately 50° C. to approximately 60° C., and cooled to room temperature. However, other organic solvents may be used. The sodium hydride may be used in Reaction 11 at from approximately 1 mole equivalent to approximately 3 mole equivalents per mole equivalent of Compound XII, such as approximately 1.2 mole equivalents. After cooling, THF or other organic solvent may be added and the sodium hydride solution cooled to −5° C. Trimethylsulfonium iodide may be added to the cooled sodium hydride solution in a single portion. The trimethylsulfonium iodide may be used in Reaction 11 at from approximately 1 mole equivalent to approximately 3 mole equivalents per mole equivalent of Compound XII, such as approximately 1.2 mole equivalents. After removing the cooling source, THF or other organic solvent may be combined with the Compound XII. The Compound XII and THF may be added to the solution containing the sodium hydride and trimethylsulfonium iodide, causing the temperature of the reaction mixture to increase. The reaction mixture may be reacted with stirring for an amount of time sufficient for the reaction to proceed to completion, during which the temperature of the reaction mixture may rise to approximately room temperature. Water may be added to the reaction mixture, followed by at least one liquid:liquid extraction, dried, filtered, and concentrated to produce Compound XIII as a colorless oil. By way of example, the reaction mixture may be poured into water and extracted with an organic solvent, such as a heptane. The organic phase layers may be washed with water and with an aqueous brine solution. An organic solvent, such as ethyl acetate, may be added and the solution dried over Na$_2$SO$_4$. The solution may filtered, such as through silica, and the filtrate concentrated, producing Compound XIII as a colorless oil. Compound XIII may be produced at a yield of greater than approximately 90%.

As shown in Reaction 12, lithium iodide may be reacted with Compound XIII to produce 6-(5-ethoxyhept-1-yl)bicyclo[3.3.0]octan-3-one as the major product. Due to the symmetry of the final product, both isomers of Compound XIII may be reacted with the lithium iodide to produce the 6-(5-ethoxyhept-1-yl)bicyclo[3.3.0]octan-3-one. The lithium iodide may be used in Reaction 12 at from approximately 1 mole equivalent to approximately 3 mole equivalents per mole equivalent of Compound XIII, such as approximately 1.2 mole equivalents. The method of the invention may produce a racemic mixture of 6-(5-ethoxyhept-1-yl)bicyclo[3.3.0]octan-3-one at a good yield and purity. A solution of lithium iodide in THF may be added portion-wise to a solution of Compound XIII in THF. A Lewis acid other than lithium iodide may also be used in Reaction 12. Another organic solvent may also be used in Reaction 12, such as DMSO or dichloromethane. Since the reaction is exothermic, the reaction mixture may be cooled to room temperature using an ice bath. The reaction temperature may vary between approximately 10° C. and approximately 25° C. The reaction mixture may be stirred for an amount of time sufficient for the reaction to proceed to completion, such as from approximately one hour to approximately three hours. Once the reaction has proceed to completion, water may be added and the reaction mixture subjected to at least one liquid:liquid extraction with an organic solvent, such as a heptane. The organic phase layers may be washed, dried, filtered, and purified to produce 6-(5-ethoxyhept-1-yl)bicyclo[3.3.0]octan-3-one as an oil. By way of example, water may be added to the reaction mixture and the reaction mixture extracted with heptanes. The organic phase layers may be washed with an aqueous brine solution, dried over Na$_2$SO$_4$, and filtered through silica. The silica may be rinsed with 20% ethyl acetate in heptanes, which are concentrated to provide 6-(5-ethoxyhept-1-yl)bicyclo[3.3.0]octan-3-one as an oil. The oil may be further purified by chromatography to produce pure 6-(5-ethoxyhept-1-yl)bicyclo[3.3.0]octan-3-one at a yield of greater than approximately 20%, such as greater than approximately 40%. The 6-(5-ethoxyhept-1-yl)bicyclo[3.3.0]octan-3-one may have a purity of greater than approximately 99% by gas chromatography coupled mass spectroscopy (GC/MS) analysis. The 6-(5-ethoxyhept-1-yl)bicyclo[3.3.0]octan-3-one may have a purity of greater than approximately 95% by nuclear magnetic resonance (NMR) analysis and greater than 85% by chiral gas chromatography (GC) analysis.

A similar method may also be used to synthesize 6-(5-methoxyhept-1-yl)bicyclo[3.3.0]octan-3-one or CYOCTOL™. CYOCTOL™ is a derivative of ETHOCYN® having a methoxy group at the C-5 position rather than an ethoxy group. The CYOCTOL™ may be synthesized in a manner similar to that described above.

If additional purification of the 6-(5-ethoxyhept-1-yl)bicyclo[3.3.0]octan-3-one is desired, the purification may achieved by conventional techniques, such as by chromatography.

Since 6-(5-ethoxyhept-1-yl)bicyclo[3.3.0]octan-3-one has four chiral centers, the 6-(5-ethoxyhept-1-yl)bicyclo[3.3.0]octan-3-one synthesized by the method of the invention may, theoretically, include up to sixteen different isomers. However, the two five-membered rings in 6-(5-ethoxyhept-1-yl)bicyclo[3.3.0]octan-3-one are cis-fused because the two chiral centers at C-3a and C-6a are linked to each other. Therefore, the method of the invention may produce a racemic mixture of up to eight different isomers of 6-(5-ethoxyhept-1-yl)bicyclo[3.3.0]octan-3-one.

In some embodiments, the chemical compound 6-(5-ethoxyhept-1-yl)bicyclo[3.3.0]octan-3-one produced as described above may be formulated into a composition suitable for topical administration, such as a pharmaceutical composition or a cosmetic composition. By way of example, the 6-(5-ethoxyhept-1-yl)bicyclo[3.3.0]octan-3-one may be formulated into a salve, cream, ointment, lotion, gel, foam, dispersant, mousse, solution, aerosol, suspension, or emulsion. The 6-(5-ethoxyhept-1-yl)bicyclo[3.3.0]octan-3-one may also be incorporated into a variety of cosmetic products including, but not limited to, solid, semi-solid, and liquid make-up (e.g., foundations, eye makeup, and lip treatments), make-up remover, deodorants and antiperspirants, soaps, bath products (e.g., oils or salts), hair care products, sunscreen, shaving lotions, and baby products. The 6-(5-ethoxyhept-1-yl)bicyclo[3.3.0]octan-3-one may also be formulated into a composition suitable for oral administration, such as a tablet or capsule.

The 6-(5-ethoxyhept-1-yl)bicyclo[3.3.0]octan-3-one may be present in the composition at a therapeutically effective amount, which is the amount of the compound that, when administered to a patient for treating or preventing a medical disorder or condition, is sufficient to effect such treatment or prevention of the medical disorder or condition. In certain embodiments, the 6-(5-ethoxyhept-1-yl)bicyclo[3.3.0]octan-3-one may be present in the composition at a concentration of from approximately 0.01% by weight to approximately 5% by weight. By way of example, the 6-(5-ethoxyhept-1-yl)bicyclo[3.3.0]octan-3-one may be used to treat or prevent DHT-mediated medical disorders, such as acne vulgaris, hirsuitism, androgenetic alopecia, or keloid scars.

The composition may also include a pharmaceutically acceptable vehicle, which may function as a diluent, dispersant, or solvent. The pharmaceutically acceptable vehicle is a substance that is non-toxic, biologically tolerable, compatible with the 6-(5-ethoxyhept-1-yl)bicyclo-[3.3.0]octan-3-one, and otherwise biologically suitable for administration to a subject. The pharmaceutically acceptable vehicle is added to the composition or otherwise used as a vehicle, carrier, or diluent to facilitate administration of the 6-(5-ethoxyhept-1-yl)bicyclo[3.3.0]octan-3-one. The pharmaceutically acceptable vehicle may include, but is not limited to, water, saline, phosphate buffered saline, Hank's solution, Ringer's solution, dextrose/saline, or glucose, lactose, or sucrose solutions. The composition may also include pharmaceutically acceptable excipients, such as starch, glucose, lactose, sucrose, gelatin, malt, rice, flour, chalk, silica gel, magnesium stearate, sodium stearate, glycerol monostearate, talc, sodium chloride, dried skim milk, glycerol, propylene glycol, water, or ethanol.

The composition may, optionally, include minor amounts of other ingredients, such as absorbents, abrasives, anticaking agents, antifoaming agents, antimicrobial agents, binders, biological additives, buffering agents, bulking agents, chemical additives, cosmetic biocides, denaturants, cosmetic astringents, drug astringents, external analgesics, film formers, opacifying agents, essential oils, skin sensates, emollients, skin soothing agents, skin healing agents, plasticizers, preservatives, preservative enhancers, propellants, reducing agents, skin conditioning agents, skin penetration enhancing agents, skin protectants, solvents, suspending agents, emulsifiers, thickening agents, solubilizing agents, sunscreens, sun-blocks, ultraviolet light absorbers or scattering agents, sunless tanning agents, chelating agents, sequestrants, depilation agents, desquamation agents/exfoliants, organic hydroxy acids, or natural extracts.

The following examples serve to explain embodiments of the invention in more detail. These examples are not to be construed as being exhaustive or exclusive as to the scope of the invention.

EXAMPLES

Solvents and reagents used in the synthesis of 6-(5-ethoxyhept-1-yl)bicyclo[3.3.0]octan-3-one were purchased from commercial sources, such as from Sigma-Aldrich Co. (St Louis, Mo., US) or other chemical supply company. The solvents and reagents used were of reagent grade or higher.

Example I

Synthesis of Compound X from Compound IX

To Compound IX (35.2 g, 0.168 mol) in diethyl ether (250 ml) was added zinc powder (17.5 g, 0.268 mol). The mixture was heated just below reflux temperature. Trichloroacetylchloride (26.3 ml, 0.234 mol) was diluted with diethyl ether to 100 ml and this solution was added dropwise to the mixture including Compound IX. After approximately one minute, the reaction mixture started refluxing vigorously. The addition of the trichloroacetylchloride solution took approximately ninety minutes. After the addition was complete, stirring under reflux was continued for approximately thirty minutes. The reaction mixture was cooled to room temperature and filtered through CELITE® diatomaceous earth. The filter cake was rinsed with diethyl ether. The combined organic phase layers were washed with water twice and the organic phase layer was stirred with a saturated aqueous solution of $NaHCO_3$ for approximately one hour. After separation of the layers, the organic phase layer was washed with brine, dried over $Na_2SO_4$, filtered through a short plug of silica, and concentrated in vacuo. The residue was purified by bulb to bulb distillation, (0.03 mmHg, 180° C.-200° C.) to yield approximately 45 g of a colorless oil.

Example II

Synthesis of Compound XII from Compound X

To a solution of Compound X (30 g, 0.093 mol) in acetic acid (250 ml) was added zinc (60 g, 0.91 mol), at approximately 15° C. in small portions over approximately forty-five minutes. The temperature rose to approximately 25° C. After the addition was complete, the mixture was stirred for approximately one hour. The reaction mixture was filtered through CELITE® diatomaceous earth and the filtrate was concentrated in vacuo. The residue was partitioned between heptanes (250 ml) and water. The organic and aqueous phase layers were separated and the organic phase layer washed twice with a saturated aqueous solution of $NaHCO_3$/brine, dried over $Na_2SO_4$, and 50 ml of ethyl acetate was added. The mixture was filtered through silica and the filtrate was concentrated. The residue was purified by bulb to bulb distillation, (0.02 mmHg, 140° C.) to yield approximately 14.5 g of a colorless oil (0.0575 mol, 62% yield).

Example III

Synthesis of Compound XIII from Compound XII

To DMSO (100 ml) was added NaH (2.7 g, 60% in oil, 67.4 mmol). The mixture was warmed to 55° C. and stirred for approximately 1.5 hours. After cooling the mixture to room temperature, THF was added (100 ml) and the mixture was cooled to −5° C. Trimethylsulfonium iodide (13.7 g, 67.4 mmol) was added in one portion and the mixture was stirred for approximately two minutes, during which time not all of the trimethylsulfonium iodide dissolved. The ice-methanol bath was removed and Compound XII (14.15 g, 56.15 mmol) in THF (20 ml) was added in one portion. The temperature rose to approximately 8° C. Stirring continued for approximately two hours and the temperature was allowed to rise to room temperature. The mixture was poured in water (500 ml) and extracted twice with heptanes (2×300 ml). The combined organic phase layers were washed four times with water and once with brine. Ethyl acetate (200 ml) was added and the solution was dried over $Na_2SO_4$. The mixture was filtered through a short plug of silica and concentrated, providing 14.8 g (0.0556 mol, 99% yield) of Compound XIII as a colorless oil.

Example IV

Synthesis of 6-(5-ethoxyhept-1-yl)bicyclo[3.3.0]octan-3-one from Compound XIII To a solution of Compound. XIII (47.2 g, 0.177 mol) in THF (200 ml) was added a solution of lithium iodide (28.5 g, 0.212 mol) in THF (100 ml) portionwise. The addition was very exothermic and the mixture was cooled to room temperature using an ice bath. The reaction temperature varied between approximately 10° C. and approximately 25° C. The mixture was stirred for approximately two hours and poured in water (200 ml). The mixture was extracted twice with heptanes. The combined organic phase layers were washed twice with brine, dried over sodium sulfate ($Na_2SO_4$), and filtered through silica. The plug of silica was rinsed with 20% ethyl acetate in heptanes. The organic phase layers were concentrated to provide approximately 45 g of the crude product as an oil. The crude product was purified by chromatography (gradient, 0%-25% ethyl acetate in heptanes, silicyle 800 g Si cartridge), providing approximately 22 g (0.082 mol, 46% yield) of pure 6-(5-ethoxyhept-1-yl)bicyclo[3.3.0]octan-3-one. Another fraction of approximately 11 g of 6-(5-ethoxyhept-1-yl)bicyclo[3.3.0]octan-3-one was obtained of lower purity (23% yield).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of synthesizing a compound, the method comprising:
   reacting 3-(5-ethoxyhept-1-yl)cyclopentene with dichloroketene to form a first mixture comprising 7,7-dichloro-4-(5-ethoxyhept-1-yl)bicyclo[3.2.0]heptan-6-one and 6,6-dichloro-4-(5-eth-oxyhept-1-yl)bicyclo[3.2.0]heptan-7-one;
   reacting the first mixture with acetic acid and zinc to form a second mixture comprising 4-(5-ethoxyhept-1-yl)bicyclo[3.2.0]heptan-6-one and 4-(5-ethoxyhept-1-yl)bicyclo[3.2.0]heptan-7-one;
   reacting the second mixture with trimethylsulfonium iodide to form a third mixture comprising 2-(5-ethoxyhept-1-yl)spiro[bicyclo[3.2.0]heptane-6,2'-oxirane] and 4-(5-ethoxyhept-1-yl)-spiro-[bicyclo-[3.2.0]heptane-6,2'-oxirane]; and
   reacting the third mixture with lithium iodide to form 6-(5-ethoxyhept-1-yl)bicyclo[3.3.0]octan-3-one.

2. The method according to claim 1, wherein reacting 3-(5-ethoxyhept-1-yl)cyclopentene with dichloroketene to form a first mixture comprises reacting the 3-(5-ethoxyhept-1-yl)cyclopentene with trichloroacetyl chloride and zinc.

3. The method according to claim 2, wherein reacting the 3-(5-ethoxyhept-1-yl)cyclopentene with trichloroacetyl chloride and zinc to form a first mixture comprises dissolving 3-(5-ethoxyhept-1-yl)cyclopentene in an organic solvent, dissolving zinc powder in the organic solvent, and adding a solution of trichloroacetyl chloride to the organic solvent.

4. The method according to claim 2, wherein reacting the 3-(5-ethoxyhept-1-yl)cyclopentene with trichloroacetyl chloride and zinc to form a first mixture comprises reacting reagents consisting of 3-(5-ethoxyhept-1-yl)cyclopentene, trichloroacetyl chloride, and zinc.

5. The method according to claim 1, wherein reacting 3-(5-ethoxyhept-1-yl)cyclopentene with dichloroketene to form a first mixture comprising 7,7-dichloro-4-(5-ethoxyhept-1-yl)bicyclo[3.2.0]heptan-6-one and 6,6-dichloro-4-(5-ethoxyhept-1-yl)bicyclo[3.2.0]heptan-7-one comprises filtering and concentrating the first mixture comprising 7,7-dichloro-4-(5-ethoxyhept-1-yl)bicyclo[3.2.0]heptan-6-one and 6,6-dichloro-4-(5-ethoxyhept-1-yl)bicyclo[3.2.0]heptan-7-one.

6. The method according to claim 1, wherein reacting the first mixture with acetic acid and zinc to form a second mixture comprises reacting the first mixture with acetic acid and zinc without distilling the first mixture.

7. The method according to claim 1, wherein reacting the second mixture with trimethylsulfonium iodide to form a third mixture comprises adding trimethylsulfonium iodide, sodium hydride, and dimethylsulfoxide to the second mixture.

8. The method according to claim 1, wherein reacting the third mixture with lithium iodide to form 6-(5-ethoxyhept-1-yl)bicyclo[3.3.0]octan-3-one comprises dissolving the 2-(5-ethoxyhept-1-yl)spiro[bicyclo[3.2.0]heptane-6,2'-oxirane] and 4-(5-ethoxyhept-1-yl)spiro[bicyclo[3.2.0]heptane-6,2'-oxirane] in tetrahydrofuran and adding a solution of lithium iodide in tetrahydrofuran.

9. The method according to claim 1, wherein reacting the third mixture with lithium iodide to form 6-(5-ethoxyhept-1-yl)bicyclo[3.3.0]octan-3-one comprises filtering and concentrating the 6-(5-ethoxyhept-1-yl)bicyclo[3.3.0]octan-3-one.

10. The method according to claim 1, further comprising purifying the 6-(5-ethoxyhept-1-yl)bicyclo[3.3.0]octan-3-one.

* * * * *